United States Patent [19]

McRae

[11] Patent Number: Plant 6,501

[45] Date of Patent: Jan. 3, 1989

[54] LILY PLANT NAMED SYLPHIDE

[75] Inventor: Edward A. McRae, Boring, Oreg.

[73] Assignee: Melridge, Inc., Gresham, Oreg.

[21] Appl. No.: 27,621

[22] Filed: Mar. 18, 1987

[51] Int. Cl.[4] ..... A01H 5/00

[52] U.S. Cl. ..... Plt./68

[58] Field of Search ..... Plt. 68

*Primary Examiner*—James R. Feyrer

*Attorney, Agent, or Firm*—Charles W. Rummler

[57] ABSTRACT

A new variety of hybrid lily plant bearing large upright to semi-upright flowers particularly characterized by their unspotted, pure white coloration with a soft pink reverse side. The flowers of this new plant are of excellent form and with their large size and substance, orientation and color, provide a combination that is completely new in the Oriental hybrid divisions of lilies suited to forcing and mass commercial cultivation. The plant is highly resistant to disease, shows tolerance of virus, and is an excellent garden plant. The bulbs of this plant may be precooled and forced for cut flower production, the resulting clone being vigorous, a good grower, and an excellent propagator.

1 Drawing Sheet

BACKGROUND OF THE INVENTION

My new variety of lily plant originated as a seedling which first flowered at Sandy, Oreg., in 1970 and is one of a group of seedlings planted by me with the object of producing large flowered, upright and semi-upright Oriental hybrids in shades of soft pink and white suited to forcing into flower out-of-season, heretofore unknown in the lily breeding art. The mother plant for these seedings was a hybrid produced by my crossing a clonal selection from the 'Pink Glory' strain with a selected form of the species *Lilium nobilissimum,* which was done in a greenhouse maintained with extremely high temperatures for at least one week after pollination, this procedure being necessary in order to successfully cross these distantly related lilies for the production of the seeds planted to produce the new seedling. This particular seedling was selected by me for propagation because of the large size and upright orientation of its flowers and its broad tepalled, bowl-shaped form, unusually thick substance, and a distinctive unspotted pure white top side tepal coloration and having a soft pink reverse side, a combination unique among Oriental hybrid lilies. Also, the selected seedling possessed unusually strong, stout stems with extremely broad leaves.

This selected seedling was asexually reproduced by me and under my direction at Sandy, Oreg., by bulb scale propagation, with such satisfactory results that propagation was carried on at Sandy, Oreg., through several successive generations by bulb scale propagation as well as by natural propagation from bulblets. The successive generations of this new plant have demonstrated that the clones thereof possess to a high degree the novel characteristics of the original seedling, as well as the desirable characteristics of hybrid vigor, great hardiness, and disease resistance, and that these characteristics hold true from generation to generation under asexual propagation and appear to be firmly fixed.

DESCRIPTION OF THE DRAWING

This new variety of lily plant is illustrated by the accompanying photographic drawing, which shows a full face view of the open bloom in full color and illustrates the flower form and tepal arrangement and in particular, the novel and distinctive unspotted pure white coloration of the flower.

DESCRIPTION OF THE NEW VARIETY

The following is a detailed description of my new variety of Asiatic hybrid lily with nomenclature according to The International Lily Register of The Royal Horticultural Society of London (2nd edition, 1969), and with the color designations according to The R.H.S. Colour Chart published in 1966 by The Royal Horticultural Society.

THE PLANT

Origin: Seedling.

Parentage:

- *Seed parent.*—A selected clone from the Pink Glory strain.
- *Pollen parent.*—A selected clone of *Lilium nobilissimum.*

Classification:

- *Horticultural.*—Division VII-B, bowl-shaped Oriental hybrid lily, according to The Horticultural Classification of Lilies by The Royal Horticultural Society of London.
- *Commercial.*—Hybrid Lilium Clone.

Form: Single stem, erect and stately.

Height: About 70 to 125 cm. from bulbs of about 14 to 18 cm. in circumference, provided their light levels are adequate. Low light levels may cause "stretching".

Growth: Vigorous and upright.

Foliage:

- *Quantity.*—Abundant.
- *Leaf size.*—Unusually broad, about 7 to 8 cm. wide and about 12 to 15 cm. long.
- *Leaf shape.*—Generally ovate with acuminate tip.
- *Texture.*—Leathery.
- *Aspect.*—Glossy.
- *Color.*—Medium green, lighter on the lower side.

Bulbs:

- *Size.*—Various and ranging up to 25 cm. in circumference in commercial use.
- *Color.*—White with flushes of soft pink or soft yellow after exposure to light.

THE BUD

Form: Long ovoid with rounded base and obtuse tip.

Size: About 9 to 12 cm. long and about 10 to 12 cm. in circumference just prior to opening.

Opening rate: The bud opens slowly, taking about an hour in response to morning light.

Color: Soft pink with deeper midribs, overlaying soft green.

Peduncle:

*Length.*—Averages about 4 to 6 cm., but may elongate if light levels are too low or if bulbs have been improperly stored prior to forcing.

*Color.*—Medium green with an overlay of very light plum.

THE FLOWER

Blooming habit: Once annually and profusely in midseason.

Size: Large; averaging about 18 to 23 cm. in diameter, reflexing at the tips on the second day to a spread of about 15 to 18 cm. in diameter.

Tepalage:

*Number.*—Six, hexagonally arranged and imbricated.

*Size.*—Outer tepals — About 3 to 3.5 cm. wide. Inner tepals — About 5 to 5.5 cm. wide.

Borne: As a raceme on a single stem having three to six flowers from a bulb of about 14 to 16 cm. in circumference.

Shape: As a broad bowl by the second day, with the "bowl" about 10 cm. deep.

Color: The flowers are distinguished by their pure white coloration. Under unusually cool, bright conditions, soft flushes of pale pink may occasionally appear on the tepals. The nectary furrows are apple green and the reverse sides of the tepals are a soft pink.

Aspect: The flower is shiny.

Spotting: The flowers are completely unspotted.

Longevity: The tepals stay on the stems about three weeks.

Pedicel:

*Length.*—In average, about 8 to 12 cm.

*Form.*—Sturdy and ascending up to about 45 degrees from the horizontal.

*Color.*—Medium green with very light plum overlay.

Disease resistance: The flower and plant are resistant to disease; in particular, they are resistant to Fusarium bulb rot and Botrytis blight, as observed in western Oregon.

Fragrance: Heavy.

Lasting quality: The flower is long lasting, both on the plant and as a cut flower.

REPRODUCTIVE ORGANS

Stamens:

*Number.*—Six.

*Arrangement.*—Typical of the genus Lilium.

*Anthers (dehisced)* and pollen.—Color: Grayed red, 179A.

*Filaments.*—Length: About 8 to 10 cm. Color: Soft green to white.

Pistil:

*Number.*—One.

*Style.*—About 8 to 10 cm. long.

*Stigma.*—Color: Soft greenish-white to very light pink. Size: Large.

*Ovary.*—Characteristic of genus Lilium.

THE FRUIT

Fertility: The fruit is fertile.

Shape: Ovoid.

Color at maturity: Soft brown, sometimes overlaid with soft plum.

This new hybrid Oriental lily most nearly resembles *Lilium nobilissimum* (unpatented) but is taller with stronger stems and its buds and flowers have a soft pink reverse side coloring, unlike *Lilium nobilissinum.* The flowers of the new variety are not as completely upfacing as those of *Lilium nobilissimum* and its flower form is larger, conspicuously broader tepalled, and more bowl-shaped and less trumpet-formed than *Lilium nobilissimum.*

I claim:

1. The new and distinctive variety of Oriental hybrid lily plant and parts thereof, substantially as herein shown and described, characterized by the pure white unspotted coloration of the flowers and the excellence of the flower form, size, and substance; by the unique upright to semi-upright orientation of the flowers; and by its versatility both as a garden plant and as a cut flower producer.

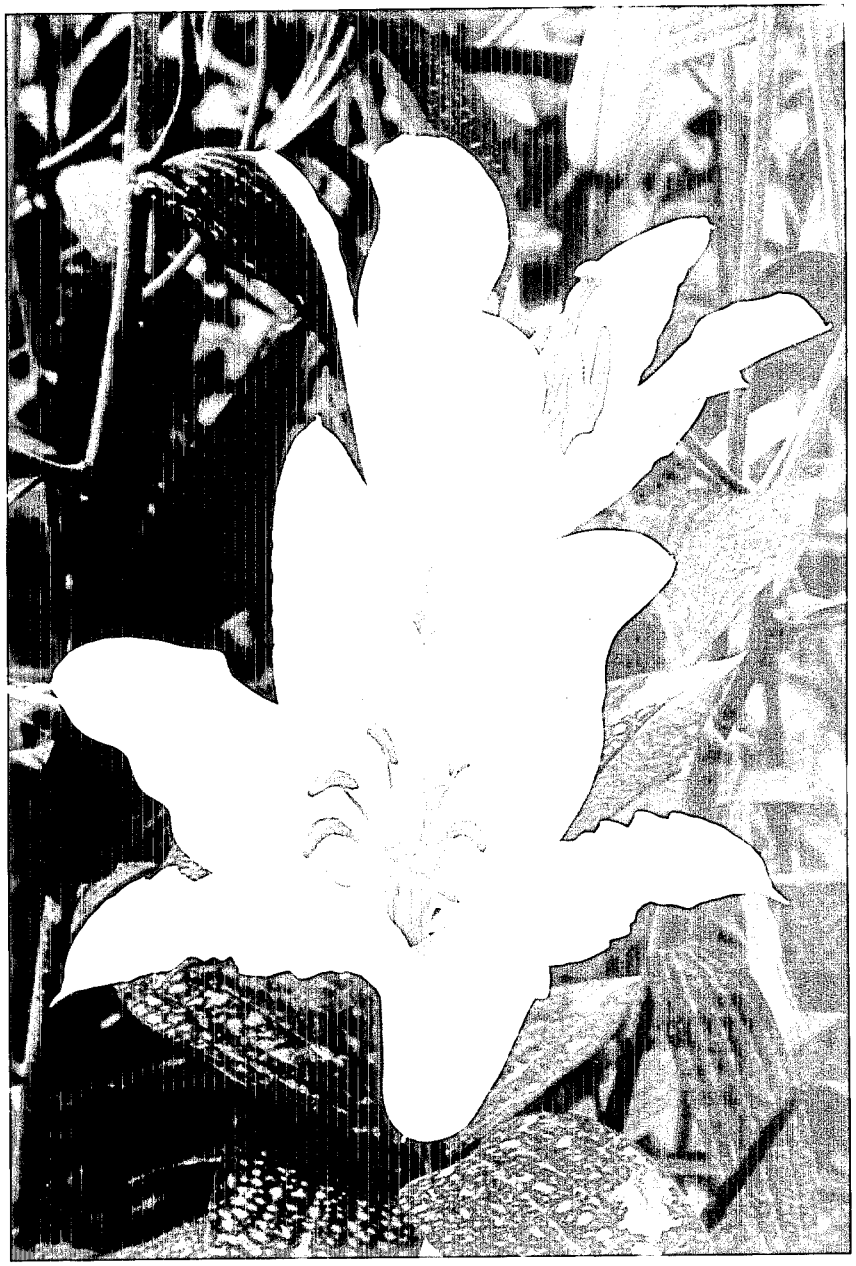

* * * * *